United States Patent [19]
Wood

[11] Patent Number: 5,604,262
[45] Date of Patent: Feb. 18, 1997

[54] TOPICAL ANTIMICROBIAL AGENTS

[75] Inventor: William F. Wood, McKinleyville, Calif.

[73] Assignee: Research Corporation Technologies, Inc., Tucson, Ariz.

[21] Appl. No.: 408,913

[22] Filed: Mar. 22, 1995

[51] Int. Cl.$^6$ .................................................. A61K 31/12
[52] U.S. Cl. ........................ 514/675; 424/405; 568/303
[58] Field of Search .............................. 424/59, 60, 405; 514/675; 568/303

[56] References Cited

U.S. PATENT DOCUMENTS 4,692,329  9/1987  Klein et al. .............................. 424/81
4,896,768  1/1990  Anderson ............................... 206/210

OTHER PUBLICATIONS

Vincenzo Amico et al., "Antimicrobial Tetraprenyltoluquinol Derivatives from *Cystoseira Spinosa Var. Squarrosa*," *Phytochemistry*, 27, 1327–1331 (1988).
Vincenzo Amico et al., "Three Acetogenins from the Brown Alga *Caulocystis Cephalornithos*," *Journal of Natural Products*, 53, 1379–1382 (Sep.–Oct. 1990).
B. Banaigs et al., "Diterpenoid Metabolites from the Marine Alga Cystoseira Elegans," *Tetrahedron*, 39, 629–638 (1983).
Michel Barbier, "129. Cyclizations of the $C_{10}$ Fatty Acids from the Mandibulary Glands of the Honeybee *Apis mellifica L.*: Queen Substance and Royal Jelly Acid," *Helvetica Chimica Acta*, 64, 1407–1413 (1981).
M. Baxter et al., "The Effect of Fatty Materials Extracted From Keratins on the Growth of Fungi, With Particular Reference to the Free Fatty Acid Content," *Sabouradia*, 7, 199–206 (1969).
Bobby L. Bowles et al., "Antibotulinal Properties of Selected Aromatic and Aliphatic Ketones," *Journal of Food Protection*, 56, 795–800 (Sep. 1993).
B. V. Burger et al., "Mammalian Pheromones VIII—Chemical Characterization of Preorbital Gland Secretion of Grey Duiker, *Sylvicapra grimmia* (Artiodactyla: Bovidae)," *Journal of Chemical Ecology*, 16, 397–416 (1990).
Allan A. Croteau et al., "A Convenient Route to α,β–Unsaturated Methyl Ketones Application to Retinal Analogue Synthesis," *Tetrahedron Letters*, 24, 2481–2484 (1983).
S. K. Das et al., "Effect of Undecanoic Acid on Phospholipid Metabolism in *Trichophyton Rubrum*," *Sabouraudia*, 20, 267–272 (1982).
Z. Duvnjak et al., "The Influence of Fatty Acids on the Growth of ((Candida Tropicalis)) in the Presence of Alkanes," *Ann. Inst. Pasteur*, 122, 987–1007 (1972).
Nils Fries, "The Growth-Promoting Activity of Some Aliphatic Aldehydes on Fungi," *Sy. Bot. Tidskr.*, 55, 1–16 (1961).
A. P. Garg et al., "Inhibition of Growth of Keratinophilic Fungi by Oils and Fatty Acids," *Trans. Br. mycol. Soc.*, 85, 367–370 (1985).
A. P. Garg et al., "Fungitoxicity of Fatty Acids Against Dermatophytes," *Mycoses*, 36, 51–63 (1993).

Herman Gershon et al., "Antifungal Properties of n–Alkoxyacetic Acids and Their Methyl Esters," *Journal of Pharm. Sciences*, 68, 82–84 (Jan. 1979).
Li–Biao Han et al., "Synthesis of Enones and Cyclopropanes by the Reaction of Telluronium Ylides Generated from Bis(2–oxoalkyl)tellurium Dichlorides," *Chemistry Letters*, 561–564 (1993).
Yao–Zeng Huang et al., "α–Enone by the Reaction of Aldehyde and α–Bromoketone with Tri–n–Butylstibine$^1$," *Synthetic Communications*, 19, 501–509 (1989).
N. Jabri et al., "Palladium Mediated Synthesis of Conjugated E or Z Enones and Unsymmetrical Divinyl Ketones. One–Pot Preparation of Isoegomaketone," *Tetrahedron*, 42, 1369–1380 (1986).
A. M. Janssen et al., "Antimicrobial Activity of Essential Oils: A 1976–1986 Literature Review. Aspects of the Test Methods," *Planta Medica*, 53, 395–398 (Aug. 1987).
Jahyo Kang et al., "Hydroacylation of Alkynes with Alkylpentacarbonylchromate Anions," *Bull. Korean Chem. Soc.*, 15, 306–310 (1994).
Rymantas Kazlauskas et al., "New Metabolites from the Brown Alga *Caulocystis cephalornithos*," *Aust. J. Chem.*, 33, 2097–2101 (1980).
Edmund L. Keeney et al., "Propionate and Undecylenate Ointments in the Treatment of Tinea Pedis and an In Vitro Comparison of Their Fungistatic and Antibacterial Effects with other Ointments," *Bull. Johns Hopkins Hosp.*, 75, 417–439 (1944).
Kologrivova et al., "Oxidation of α,β–Unsaturated Methyl Ketones by Sodium Hypobromite," *Zh. Obshch, Khim.*, 28, 1269–1273 (1957).
Kiyosi Kondo et al., "Sulfonyl Carbanions in Synthesis. I. A Novel Route to α,β–Unsaturated Carbonyl Compounds," *Tetrahedron Letters*, 12, 1007–1010 (1975).
Takuo Kosuge et al., "An Antifungal Constituents of Rice Bran Tar," *Yakugaku Zasshi*, 88, 1423–1427 (1968).
Isao Kubo et al., "Antibacterial Activity of Long-Chain Alcohols against *Streptococcus mutans*," *J. Agric. Food Chem.*, 41, 2447–2450 (1993).
Isao Kubo et al., "Naturally Occurring Antiacne Agents," *Journal of Natural Products*, 57, 9–17 (Jan. 1994).
V. Moleyar et al., "Antifungal Activity of Some Essential Oil Components," *Food Microbiology*, 3, 331–336 (1986).
Hisae Muroi et al., "Antimicrobial Activity of Cashew Apple Flavor Compounds," *J. Agric. Food Chem.*, 41, 1106–1109 (1993).
Herman A. Palma–Fleming et al., "Volatile Components of California Live Oak, *Quercus Agrifolia*," *Phytochemistry*, 22, 1503–1505 (1983).

(List continued on next page.)

*Primary Examiner*—Shelley A. Dodson
*Attorney, Agent, or Firm*—Schwegman, Lundberg, Woessner & Kluth, P.A.

[57] ABSTRACT

A method to inhibit microbial growth is provided comprising topically administering to a mammal afflicted with a pathology associated with microbial growth, such as a dermatological condition, an effective amount of a linear ($C_{12}$–$C_{22}$) 3-alken-2-one or 3,ω-alkadien-2-one.

20 Claims, No Drawings

OTHER PUBLICATIONS

F. G. Saitkulova et al., "Antimicrobial Activity of Aliphatic–Aromatic Ketones, β–Ketols, and α–Glycols," *Pharmaceutical Chemistry Journal*, 416–417 (Mar., 1990) (Translated from Russian Original, vol. 23, No. 5, May, 1989).

Gurdip Singh et al., "Essential Oils: A Potent Source of Natural Pesticides," *Journal of Scientific & Industrial Research*, 52, 676–683 (Oct. 1993).

I. G. Tishchenko et al., "Liquid–Phase Oxidation of α, β–Unsaturated Ketones II. Products of the Liquid–Phase Oxidation of Normal Propylidene–, Amylidene–, and Hexylidene–Acetones," *Journal of General Chemistry of the USSR*, 33, 134–137 (Jan. 1963).

Barry M. Trost et al., "Methyl 2–Pyridinesulfinate. A Convenient Reagent for Sulfinylation–Dehydrosulfinylation," *J. Org. Chem.*, 58, 1579–1581 (1993).

R. T. Yousef et al., "Evaluation of the Antifungal Activity of Some Components of Volatile Oils Against Dermatophytes," *mykosen*, 21, 190–193 (1978).

TOPICAL ANTIMICROBIAL AGENTS

BACKGROUND OF THE INVENTION

The odorous compounds of plants are volatile and are usually separated from the plant material by steam distillation. They are known as the volatile or essential oils, and consist of hydrocarbons, alcohols, ethers aldehydes and ketones. In the evaluations of conifers and in the oils from citrus fruits and from eucalyptus trees, alicyclic hydrocarbons of the composition $C_{10}H_{16}$ were found to be especially abundant, and it is to these compounds that the term "terpene" was applied in the restricted sense. It soon became evident, however, that compounds containing 15, 20, 30 and 40 carbon atoms also are closely related to terpenes, and the term "terpene" in its broadest sense now includes all such compounds, which comprise repeating iso-$C_5$ units.

Many of the essential oils are employed in various flavors and fragrances, and their medicinal or biocidal potential has been the subject of continued investigation. For example, the cyclic terpenones, α-ionone and β-ionone, were reported to exhibit moderate antibacterial activity against *S. mutans* by I. Kubo et al., *J. Agric. Food Chem.*, 41, 2447 (1993). This bacterium is responsible for causing dental caries. Carvone, the chief component of spearmint oil, was reported to exhibit antifungal activity by V. Moleyar et al., *Food Microbiol.*, 3, 331 (1986). Kubo et al., *J. Natural Products*, 57, 9 (1994) subsequently reported that a number of cyclic and acyclic terpene alcohols, including geranylacetol, farnesol and farnesyl acetol, exhibited activity against *Pr. acnes*, the bacterium responsible for acne. However, the linear ketone derived from farnesylacetol, farnesylacetone, was found to be inactive.

While some of these natural products may be potent enough for practical use, the synthesis or extraction of highly branched cyclic or alicyclic terpenes can be complex. Furthermore, terpenes such as ionone, a component of cedar oil, can cause allergic skin reactions. Nonetheless, essential oils and other phytochemicals are by definition biodegradable and renewable. Therefore, a continuing need exists for compounds of natural origin which exhibit useful levels of biocidal activity.

SUMMARY OF THE INVENTION

The present invention provides a method to inhibit the growth of microorganisms, particularly microorganisms that are responsible for mammalian skin pathologies, comprising contacting the microorganisms with an effective growth-inhibiting amount of a 3-alken-2-one of the general formula (I):

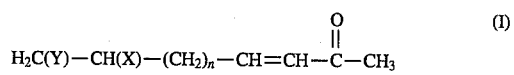

wherein n is 6–16 and X=Y=H or X and Y together are a covalent bond. Preferably n is 5–11 and X=Y=H, or n is 6–10 and X and Y together are a covalent bond. Preferably the 3,4-double bond is in the E- or trans-configuration.

Thus, the present invention also provides a composition adapted for topical application to the skin comprising an effective antimicrobial amount of at least one compound of formula (I), in combination with a dermatologically acceptable carrier. Preferred compositions in accord with the present application are therapeutic compositions adapted for topical application, as to the skin of a mammal afflicted with, or at risk of affliction with, a pathology associated with a microorganism such as a bacterium, a yeast or a fungus.

Novel compounds of formula (I) are also within the scope of the invention, including 3-hexadecen-2-one.

The term "skin" as used herein is to be construed broadly, to include the epidermis, the lips, the scalp, the epithelium of the eye, the surfaces of body cavities, including the mouth, ear, nose, vagina, anus and the like, and the surfaces of wounds or lesions in the skin. The term "antimicrobial" or "inhibit," as used with respect to the growth of microorganisms, is defined to encompass both complete inhibition (killing) of the microbes, as well as significant inhibition in growth or sporulation, as determined by the assays described herein, or by other standard assays, such as those disclosed by A. M. Janssen et al., *Planta medica*, 53, 395 (1987). Thus, the term "antimicrobial" encompasses the use of the present compounds in deodorant compositions, to control body odor, as well as in therapeutic compositions. All percentages are by weight unless otherwise noted.

DETAILED DESCRIPTION OF THE INVENTION

A. Preparation

The 3-alken-2-ones of the present invention which are not commercially available, or which are novel compounds can be prepared by a number of methods available to the art. For example, 3-alken-2-ones of general formula RCH=CH-C(O)-CH$_3$ can generally be prepared by the crossed aldol condensation of acetone and the alkanal (RCHO), followed by the acid-catalyzed elimination of water from the resultant hydroxy ketone. See, for example, B. V. Burger et al., *J. Chem. Ecol.*, 16, 397 (1990) (3-dodec-2-one) and G. Tishenko et al., *J. Gen. Chem.* USSR, 33, 134 (1963) (3-nonen-2-one). Alternatively, they can be prepared by the Wittig or Wittig-Horner reaction.

Y.-Z. Huang et al., *Synth. Commun.*, 19, 501 (1989) have also reported a general synthesis of 2-alken-2-ones (trans-RCH=CHC(O)CH$_3$) by the reaction of the aldehyde (RCHO) with α-bromoacetone in the presence of tri-n-butylstibine for 1–16 hr at 25°–50° C., and prepared compounds wherein R is n-$C_4H_9$, n-$C_8H_{17}$ or n-$C_{11}H_{23}$. The 3-alken-2-one wherein R is n-$C_{13}H_{26}$ has been reported by R. Kazlauskas et al., *Aust. J. Chem.*, 33, 2097 (1980).

The 3-alkene-2-one wherein R is $C_7H_{15}$ has been reported by H. A. Palma-Fleming et al., *Phytochem.*, 22, 1503 (1983). The 3-aken-2-one wherein R is $C_9H_{19}$, was prepared by A. A. Croteau et al., *Tet. Letters*, 24, 2481 (1983), who report a general synthesis of E/Z mixtures of 3-alken-2-ones by the condensation of lithiated α-silylketimine (Me$_3$Si-CHLi-C(=Nt-Bu)Me) with RCHO, followed by hydrolysis. Also, the preparation of (Z)-3-alken-2-ones by the condensation of alkenyl lithiocuprates with acetyl halides has been reported by N. Jabri et al., *Tetrahedron*, 42, 1369 (1986). The preparation of 3-tetradecen-2-one (R=$C_{10}H_{21}$) has been reported by J. Kang et al., *Bull. Korean Chem. Soc.*, 15, 306 (1994).

B. Bioactivity

The present compounds and compositions comprising them can be employed in a wide range of antimicrobial applications, including surface disinfecting, and for treating foods such as fruits and seeds. The present compounds are particularly useful to inhibit the growth of pathological microorganisms, such as bacteria, fungi and yeasts on the skin of humans and of animals such as household pets, farm animals and zoo animals. Such grampositive microorganisms include *Propionibacterium acnes* which is the primary pathogen which causes human acne vulgaris, and the streptocci and staphylococci which cause impetigo. Mycotic infections of animals and humans can also be treated, including tinea capitis, tinea cruris (jock itch), tinea corporis (ringworm), tinea pedis (athlete's foot) and tinea unguium. Fungi associated with such dermatophytosis include *T. mentagrophytes, M. audevinii, T. rubrum, E. floccosum, M. pelineum* and *Candida albicans*.

The present compounds are also effective against fungi associated with infections of the membranes of body cavities. Such infections include thrush, vaginitis and paronychia. See R. T. Yousef et al., *Mykosen,* 21, 190 (1978) and H. Gershon, *J. Pharm. Sci.,* 68, 82 (1979). The present compounds can also be used in cosmetic and skin-cleansing compositions such as soaps, shampoos, deodorants, and skin softening lotions, where they can function as deodorants, i.e., to control odor-causing bacteria on the skin. The present compounds can also be employed in dentifrices, chewing gums, and mouthwashes to inhibit the growth of *Streptococcus mutans,* which is a causative agent for dental caries, and in shampoos, rinses, and other haircare products, to inhibit *Pityrosporum ovale* (dandruff, skin lesions in immune-suppressed subjects). Infections due to *Staphylococcus aureus* are also susceptible to these compounds.

C. Compositions.

Although in some instances, the present compounds may be administered in pure form, i.e., when they are liquids, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as flavorings, fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. The liquid compositions can also be employed as eyedrops, mouth washes, douches, etc. Antibacterial presaturated wipes are disclosed by Anderson (U.S. Pat. No. 4,896,768).

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The total concentration of one or more compounds of formula (I) in the present compositions can be varied widely, and will depend on factors such as the compatibility of the active ingredient(s) with the vehicle, the potency of the active ingredient(s) and the condition to be treated. Generally, the concentration of the compound(s) of formula (i) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The present compounds of formula (I) are particularly useful to treat human or animal acne by topical application, as gels, ointments, lotions, soaps, and the like. For a further discussion of the pathology and etiology of acne, and of the formulation of aqueous cream and gel vehicles as carriers for other agents used to treat acne, see Klein et al. (U.S. Pat. No. 4,692,329). The total dosage delivered will depend on the extent of the infected area to be treated, the severity of the infection and the number of applications, as determined by the subject's dermatologist, physician or veterinarian.

The present invention will be further described by reference to the following detailed examples.

EXAMPLE 1

Synthesis of (E)-3-Alken-2-ones and (E)-3,13-Tetradecadien-2-one

To 5.0 g of piperidine, 5.0 g of glacial acetic acid and. 250 mL of acetone at reflux in a 500 mL round-bottomed flask was added 0.10 mole of one of the following aldehydes (octanal, nonanal, decanal, undecanal, 10-undecenal, dodecanal, tridecanal, or tetradecanal) in 50 mL of acetone dropwise over 0.5 hours. After addition, the solution was refluxed for an additional 5 hours. The acetone was removed in vacuo and the residue was placed in 50 mL of diethyl ether. The ether solution was washed with 2×50 mL water, 2×50 mL 1M HCl and 2×50 mL saturated $NaHCO_3$. The ether solution was dried with anhydrous $CaCl_2$ and the ether was removed in vacuo. A pure sample of each compound was obtained by preparative gas chromatography.

EXAMPLE 2

Spectral Data for (E)-3-Alken-2-ones and (E)-3,13-Tetradecadien-2-one

Mass spectra of the following compounds were recorded on a Hewlett-Packard gas chromatograph (Model 5890) fitted with a mass selective detector (Model 5970) using a 12 m cross-linked methyl silicone capillary column. The gas chromatograph was programmed so the oven temperature was kept at 40° C. for 4 minutes, then increased to a final temperature of 250° C. at a rate of 30° C./min and kept at this temperature for four minutes. Mass spectral fragments below m/z=35 were not recorded. The mass selective detector was tuned using perfluorotributylamine and the internal computer tuning program.

The $^1H$ and $^{13}C$ NMR spectra of the compounds were recorded at 300 MHz and 75 MHz respectively on Bruker QE plus. Samples were dissolved in $CDCl_3$, and chemical shifts are given in ppm relative to tetramethylsilane (TMS) at zero ppm using the solvent peak a 77.0 ppm as the internal standard. The synthetic 3-alken-2-ones and 3,13-tetradecadien-2-one were shown to be the (E)-isomer by the $^1H$-NMR coupling constant of 15.9 Hz for the olefinic protons.

A. (E)-3-Undecen-2-one (1). 300 MHz $^1H$-NMR ($CDCl_3$)δ=6.78(dt,1H,J=15.9 Hz,6.9 Hz), 6.03(dt, 1H,J=15.9 Hz,J=1.48 Hz), 2.21(s,3H), 2.19(quart,2H), 1.44(m, 2H), 1.26(m,8H) and 0.85(t,3H); 75 MHz $^{13}C$-NMR ($CDCl_3$) δ=198.74, 148.68, 131.29, 32.50, 31.75, 29.17, 29.08, 28.12, 26.82, 22.65, 14.09; and El-MS m/z=97(7), 83(5), 81(6), 71(15), 69(18), 68(6),55(50). 43(100), 41(40) and 39(19).

B. (E)-3-Dodecen-2-one (2). 300 MHz $^1H$-NMR ($CDCl_3$) δ=6.73(dt,1H,J=15.9 Hz,6.9 Hz), 5.99(dt,1H,J=15.9 Hz,J=1.48 Hz), 2.18(s,32.15(quart,2H), 1.38(m,2H), 1.21(m, 10H) and 0.81(t,3H); 75 MHz $^{13}C$-NMR ($CDCl_3$) δ=198.80, 148.72, 131.31, 32.53, 31.87, 29.39, 29.23, 28.13, 26.84, 22.69, and 14.13; and E1-MS m/z=97(15), 83(11), 82(9), 81(8), 71(25), 69(18), 55(50), 43(100), 41(37) and 36(18).

C. (E)-3-Tridecen-2-one (3). 300 MHz $^1$H-NMR (CDCl$_3$) δ=6.81(dt, 1H,J=15.9 Hz,6.9 Hz), 6.06(dt, 1H,J=15.9 Hz,J=1.48 Hz), 2.24(s,3H), 2.22(quart,2H), 1.46(m,2H), 1.26(m, 12H) and 0.88(t,3H); 75 MHz $^{13}$C-NMR (CDCl$_3$) δ=198.80, 148.69, 131.24, 32.47, 31.85, 29.46, 29.37, 29.27, 29.17, 28.07, 26.79, 22.65, and 14.09; E1-MS m/z=196(M$^+$,2), 181(8), 97(31), 96(14), 83(22), 81(20), 71(34), 69(31), 55(65), 43(100), 41(44); and FT-IR (neat) 2925, 2854, 1700, 1677, 1628, 1467, 1360, 1253, 1189 and 980 cm$^{-1}$.

D. (E)-3-Tetradecen-2-one (4). 300 MHz $^1$H-NMR (CDCl$_3$) δ=6.79(dt,1H,J=15.9 Hz,6.9 Hz), 6.05(dt,1H,J=15.9 Hz,J=1.48 Hz), 2.23(s,3H), 2.21(quart,2H), 1.45(m, 2H), 1.26(m, 14H) and 0.87(t,3H); 75 MHz $^{13}$C-NMR (CDCl$_3$) δ=198.79, 148.71, 131.31, 32.53, 31.94, 29.62, 29.57, 29.43, 29.36, 29.23, 28.13, 26.84, 22.72, and 14.15; E1-MS m/z=97(21), 84(9), 83(8), 81(12), 71(30), 69(18), 55(50), 43(100), 41(50) and 39(18).

E. (E)-3,13-Tetradecadien-2-one (5). 300 MHz $^1$H-NMR (CDCl$_3$) δ=6.80(dt,1H,J=15.9 Hz,6.9 Hz), 6.06(dt,1H,J=15.9 Hz,J=1.48 Hz), 5.80(m,1H), 4.95(m,2H), 2.24(s,3H), 2.22(quart,2H), 2.03(quart,2H), 1.46(m,2H) and 1.28(m, 10H); 75 MHz $^{13}$C-NMR (CDCl$_3$) δ=198.83, 148.71,139.18, 131.32, 114.20, 33.83, 32.52, 29.38, 29.21, 29.12, 28.94, 28.13, 26.87; E1-MS m/z=97(20), 95(14), 81(21), 71(19), 69(17), 67(23), 55(59), 43(100), 41(71) and 39(35).

F (E)-3-Pentadecen-2-one (6). 300 MHz $^1$H-NMR (CDCl$_3$) δ=6.80(dt, 1H,J=15.9 Hz,6.9 Hz), 6.05(dt, 1H,J=15.9 Hz,J=1.48Hz), 2.23(s,3H), 2.21(quart,2H), 1.46(m, 2H), 1.26(m, 16H) and 0.88(t,3H); 75 MHz $^{13}$C-NMR (CDCl$_3$) δ=198.79, 148.71, 131.31, 32.53, 31.96, 29.66, 29.57, 29.44, 29.38, 29.33, 29.24, 28.14, 26.85, 22.73, and 14.16; E1-MS m/z=97(18), 84(10), 81(11), 71(28), 69(16), 68(10), 67(10), 55(46), 43(100), and 41(40).

G. (E)-3-Hexadecen-2-one (7). 300 MHz $^1$H-NMR (CDCl$_3$) δ=6.80(dt,1H,J=15.9 Hz,6.9 Hz), 6.06(dt,1H,J=15.9 Hz,J=1.48 Hz), 2.24(s,3H), 2.22(quart,2H), 1.47(m, 2H), 1.26(m,18H) and 0.88(t,3H); 75 MHz $^{13}$C-NMR (CDCl$_3$) δ=198.83, 148.74, 131.31, 32.54, 31.97, 29.71, 29.68, 29.58, 29.54, 29.44, 29.41, 29.25, 28.15, 26.85, 22.74, and 14.17; E1-MS m/z=97(18), 84(8), 83(8), 82(8), 81(9), 71(30), 69(15), 55(42), 43(100), and 41(50).

H. (E)-3-Heptadecen-2-one (8). 300 MHz $^1$H-NMR (CDCl$_3$) δ=6.80(dt,1H,J=15.9 Hz,6.9 Hz), 6.07(dt,1H,J=15.9 Hz,J=1.48 Hz), 2.24(s,3H), 2.22(quart,2H), 1.47(m, 2H), 1.26(m,20H) and 0.88(t,3H); 75 MHz $^{13}$C-NMR (CDCl$_3$) δ=198.83, 148.74, 131.32, 32.54, 31.97, 29.70, 29.58, 29.44, 29.41, 29.34, 29.25, 28.15, 26.87, 22.74, and 14.18; and E1-MS m/z=252 (M+, 3), 97(19), 84(8), 83(10), 81(11), 71(28), 69(14), 55(39), 43(100), and 41(50).

EXAMPLE 3

Bioassays

The microorganisms tested were from the American Type Culture Collection (Rockville, Md.). They are *Bacillus subtilis* ATCC 9372, *Brevibacterium ammoniagenes* ATCC 6872, *Staphylococcus aureus* ATCC 12598, *Streptococus mutans* ATCC 25175, *Propionibacterium acnes* ATCC 11827, *Pseudimonas aeruginosa* ATCC 10145, *Enterobacter aerogenes* ATCC 13048, *Eschericia coli* ATCC 9637, *Proteus vulgaris* ATCC 133315, *Saccharomyces cerevisiae* ATCC 7754, *Candida utilis* ATCC 9226, *Pityrosporum ovale* ATCC 14521, *Penicillium chrysogenum* ATCC 10106 and *Trichophyton mentagrophytes* ATCC 18748.

The bacterial culture media except for *S. mutans* was 0.8% nutrient broth (BBL), 0.5% yeast Extract (Difco) and 0.1% glucose (NYG broth). *S. mutans* was cultured in 3.7% brain heart infixsion broth (Difco). All fungi, except *P. ovale* and *T. mentagrophytes* were cultured in a 2.5% malt extract broth (BBL). *P. ovale* was cultured in 1% bactopeptone (Difco), 0.5% yeast extract, 1% glucose and 0.1% corn oil. For *T. mentagrophytes* the culture media was 1% bactopeptone and 4% glucose.

Freeze dried samples were prepared for testing as follows. *B. subtilis, S. cerevisiae, C. utilis,* and *P. ovale*, were shake-cultured for two days at 30° C. *P. chrysogenum* and *T. mentagrophytes* were shake-cultured for 5 days at 30° C. *B. ammoniagenes* and *E. aerogenes* were stationarily cultured at 30° C. *S. aureus, S. mutans, P. acnes, P. aeruginosa, E. coli* and *P. vulgaris* were stationarily cultured at 37° C.

The minimum inhibitory concentration (MIC) of the 3-alken-2-ones (compounds 1-4, 6-8) and 3,13-tetradecadien-2-one (compound 5) was performed using a two-fold serial broth dilution. Each test compound was dissolved in DMF and 30 µL of this sample was dissolved in 3 mL of the applicable medium. A 30 µL sample of the previously described culture of each microorganism was added to the various medium solutions. After two days, the cultures of *B. subtilis, S. cerevisiae, C. utilis B. ammoniagenes, E. aerogenes, S. aureus, S. mutans, P. acnes, P. aeruginosa, E. coli* and *P. vulgaris* were examined for turbidity (OD at 660 nm). The fungi, *P. ovale, P. chrysogenum* and *T. mentagrophytes*, were examined visually for growth at 3 days (*P. ovale*) and 5 days (*P. chrysogenum* and *T. mentagrophytes*). The MIC was determined as the lowest concentration for each compound that no growth was observed. The highest concentration used in these tests was 800 µg/mL.

TABLE 1

| | MIC of (E)-3-Alken-2-ones and (E)-3,13-tetradecadien-2-one (µg/mL) | | | | | | | |
|---|---|---|---|---|---|---|---|---|
| | Compound Tested | | | | | | | |
| Organism | 1 | 2 | 3 | 4 | 5 | 6 | 7 | 8 |
| *Bacillus subtilis* ATCC 9372 | 100 | 100 | 100 | >800 | >800 | >800 | >800 | >800 |
| *Brevibacterium ammoniagenes* ATCC 6872 | 200 | 100 | 100 | >800 | >800 | >800 | >800 | >800 |
| *Staphylococcus aureus* ATCC 12598 | 200 | 100 | 50 | >800 | >800 | >800 | >800 | >800 |
| *Streptococus mutans* ATCC 25175 | 100 | 50 | 25 | 25 | 25 | 200 | 400 | 800 |
| *Propionibacterium acnes* ATCC 11827 | 50 | 25 | 12.5 | 12.5 | 12.5 | 6.25 | 3.13 | 3.13 |
| *Pseudimonas aeruginosa* ATCC 10145 | >800 | >800 | >800 | >800 | >800 | >800 | >800 | >800 |
| *Enterobacter aerogenes* ATCC 13048 | >800 | >800 | >800 | >800 | >800 | >800 | >800 | >800 |
| *Eschericia coli* ATCC 9637 | >800 | >800 | >800 | >800 | >800 | >800 | >800 | >800 |

TABLE 1-continued

MIC of (E)-3-Alken-2-ones and (E)-3,13-tetradecadien-2-one (μg/mL)

| Organism | Compound Tested | | | | | | | |
|---|---|---|---|---|---|---|---|---|
| | 1 | 2 | 3 | 4 | 5 | 6 | 7 | 8 |
| *Proteus vulgaris* ATCC 133315 | 50 | 50 | 800 | >800 | >800 | >800 | >800 | >800 |
| *Saccharomyces cerevisiae* ATCC 7754 | 800 | 800 | >800 | >800 | >800 | >800 | >800 | >800 |
| *Candia utilis* ATCC 9226 | 50 | 400 | >800 | >800 | >800 | >800 | >800 | >800 |
| *Pityrosporum ovale* ATCC 14521 | 100 | 100 | 100 | 100 | 200 | 400 | >800 | >800 |
| *Penicillium chrysogenum* ATCC 10106 | 100 | 100 | 800 | 800 | 800 | >800 | >800 | >800 |
| *Trichophyton mentagrophytes* ATCC 18748 | 100 | 100 | 25 | 12.5 | 12.5 | 800 | >800 | >800 |

As demonstrated by the data summarized in Table 1, the greatest activity observed with compounds 1–8 occurred against *P. acnes*, the primary pathogen responsible for causing human acne. Compounds 1–5 also exhibited substantial activity against *T. mentagrophytes*, the causative agent of athlete's foot and compounds 1–7 inhibited *Streptococcus mutans* (dental caries). Compounds 1–6 also exhibited somewhat lesser activity against *P. ovale* (dandruff) and compounds (1)–(3) were active against *S. aureus* and *Proteus vulgaris*. Specifically, (E)-3-tridecen-2-one (3), showed activity against all of the grampositive bacteria (*B. subtilis, B. ammoniagenes, S. aureus, S. mutans*, and *P. acnes*) in the test. It was most active against *P. acnes*, having a minimum inhibitory concentration (MIC) of 12.5 μg/mL. This compound was not active against the gram-negative bacteria, *P. aeruginosa, E. aerogenes* and *E. coli*. Activity against yeast was mixed, no activity was seen against *S. cerevisiae* and *C. utilis*, although *P. ovale* showed moderate inhibition. Weak activity was seen with fungi *P. chrysogenum*, while the fungi *T. mentagrophytes* had a MIC of 25 μg/mL.

(E)-3-tetradecen-2-one (4), showed activity against some gram-positive bacteria (*S. mutans*, and *P. acnes*) in the test. It was most active with *P. acnes* having a minimum inhibitory concentration (MIC) of 12.5 μg/mL. This compound was not active against the gram-negative bacteria, *P. aeruginosa, E. aerogenes* and *E. coli*. Activity against yeast was mixed, no activity was seen against *S. cerevisiae* and *C. utilis*, although *P. ovale* showed moderate inhibition. Weak activity was seen with fungi *P. chrysogenum*, while the fungi *T. mentagrophytes* had a MIC of 12.5 μg/mL.

The synthetic products, (E)-3-hexadecen-2-one (7) and (E)-3-heptadecen-2-one (8), were inactive to all of the bacteria and fungi in the test, except *S. mutans* and *P. acnes*. With *S. mutans* (7) was weakly active, but (7) and (8) exhibited strong activity (3.13 μg/mL) against *P. acnes*.

EXAMPLE 4

A powder composition may be prepared having the following formulation:

| | Per Canister |
|---|---|
| Compound 4 | 1.0 g |
| Talc | 99 g |

EXAMPLE 5

A lotion composition may be prepared having the following formulation:

| | Per Canister |
|---|---|
| Compound 7 | 1.0 g |
| Cetyl Alcohol | 25 g |
| Glyceryl Stearate | 25 g |
| Glycerol | 20 g |
| Water | 10 g |
| Stearyl Alcohol | 10 g |

EXAMPLE 6

A lotion composition may be prepared having the following formulation:

| | Per Canister |
|---|---|
| Compound 7 | 0.5 g |
| Compound 4 | 0.5 g |
| Cetyl Alcohol | 25 g |
| Glyceryl Stearate | 25 g |
| Glycerol | 20 g |
| Water | 10 g |
| Stearyl Alcohol | 10 g |

Other examples of useful dermatological compositions which can be used to deliver the compounds of claim 1 to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition adapted for topical application to the skin, comprising an effective antimicrobial amount of a compound of the formula (I):

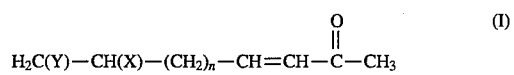

wherein n is 6–16 and X and Y are both H or together are a covalent bond, in combination with a dermatologically acceptable carrier.

2. The composition of claim 1 wherein n is 5–11 and X and Y are both H.

3. The composition of claim 1 wherein n is 6–10 and X and Y together are a covalent bond.

4. The composition of claim 1 wherein -CH=CH- is in the E-configuration.

5. The composition of claim 1 wherein the carrier is a liquid carrier.

6. The composition of claim 5 which is a solution.

7. The composition of claim 5 which is a gel.

8. The composition of claim 1 wherein the carrier is a solid carrier.

9. The composition of claim 8 wherein the solid carrier is a finely divided solid.

10. The composition of claim 9 which is a powder.

11. The composition of claim 1 which is a soap.

12. The method for inhibiting the growth of a microorganism comprising contacting said microorganism with an effective growth-inhibitory amount of a compound of formula (I):

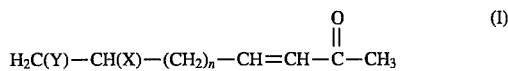

wherein n is 6–16 and X and Y are both H or together are a covalent bond.

13. The method of claim 12 wherein the microorganism is a pathogenic microorganism of mammalian skin.

14. The method of claim 13 wherein the microorganism is a pathogenic microorganism of human skin.

15. The method of claim 14 wherein the compound of formula (I) is applied topically to the skin of a human to inhibit the growth of said pathogenic microorganism.

16. The method of claim 15 wherein the pathogenic microorganism is a bacterium.

17. The method of claim 16 wherein the bacterium is *Propionibacterium acnes*.

18. The method of claim 12 wherein the bacterium is *Streptococcus mutans*.

19. The method of claim 15 wherein the microorganism is a fungus.

20. The method of claim 19 wherein the fungus is *Trichophyton mentagrophytes*.

* * * * *